(12) United States Patent
Taniguchi et al.

(10) Patent No.: US 11,469,093 B2
(45) Date of Patent: Oct. 11, 2022

(54) ULTRAVIOLET IRRADIATION APPARATUS

(71) Applicant: Ushio Denki Kabushiki Kaisha, Tokyo (JP)

(72) Inventors: Shinji Taniguchi, Tokyo (JP); Hideaki Yagyu, Tokyo (JP); Manabu Mori, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/312,589

(22) PCT Filed: Dec. 5, 2019

(86) PCT No.: PCT/JP2019/047577
§ 371 (c)(1),
(2) Date: Jun. 10, 2021

(87) PCT Pub. No.: WO2020/121934
PCT Pub. Date: Jun. 18, 2020

(65) Prior Publication Data
US 2021/0335593 A1    Oct. 28, 2021

(30) Foreign Application Priority Data

Dec. 14, 2018    (JP) .............................. JP2018-234633

(51) Int. Cl.
*H01J 65/04*    (2006.01)
*H01J 65/00*    (2006.01)
(Continued)

(52) U.S. Cl.
CPC ................ *H01J 65/00* (2013.01); *A61L 2/10* (2013.01); *H01J 61/04* (2013.01); *H01J 61/16* (2013.01); *A61L 2202/11* (2013.01)

(58) Field of Classification Search
CPC .. H01J 61/04; H01J 61/16; H01J 65/00; H01J 65/04; H01J 65/042; H01J 65/046
(Continued)

(56) References Cited

U.S. PATENT DOCUMENTS 5,514,934 A * 5/1996 Matsumoto ........... H01J 65/046
                                                 313/607
2006/0164830 A1* 7/2006 Justel .................... H01J 65/046
                                                 362/240

(Continued)

FOREIGN PATENT DOCUMENTS

CN       214012899 U  *  8/2021  ............ H01J 65/042
EP       3306641 A1      4/2018
(Continued)

OTHER PUBLICATIONS

International Search Report issued in PCT/JP2019/047577; dated Feb. 25, 2020.
(Continued)

*Primary Examiner* — Christopher M Raabe
(74) *Attorney, Agent, or Firm* — Studebaker & Brackett PC

(57) ABSTRACT

A ultraviolet irradiation apparatus includes: a first electrode block and a second electrode block located apart from each other in a first direction or located in an electrically-insulated state in the first direction; a recessed groove formed on a side surface of each of both the blocks; a first discharge lamp partially fitted into the recessed grooves formed in both the blocks and located across the both blocks; a power supply part for supplying electrical power to the first discharge lamp; a first current-carrying member electrically connecting the first electrode block and the power supply part; a second current-carrying member capable of electrically connecting the second electrode block and the power supply part at an electrical potential different from that of the (Continued)

first current-carrying member; and a light irradiation window for extracting ultraviolet light emitted from the first discharge lamp to outside.

15 Claims, 14 Drawing Sheets

(51) Int. Cl.
*A61L 2/10* (2006.01)
*H01J 61/04* (2006.01)
*H01J 61/16* (2006.01)

(58) Field of Classification Search
USPC .......................................................... 313/607
See application file for complete search history.

(56) References Cited

U.S. PATENT DOCUMENTS

| | | | | |
|---|---|---|---|---|
| 2007/0132361 | A1* | 6/2007 | Chung | H01J 65/04 |
| | | | | 313/493 |
| 2007/0159051 | A1* | 7/2007 | Byun | H01J 9/385 |
| | | | | 313/484 |
| 2007/0296327 | A1* | 12/2007 | Yano | H01J 61/305 |
| | | | | 313/485 |
| 2011/0227501 | A1 | 9/2011 | Awamoto et al. | |
| 2020/0234941 | A1 | 7/2020 | Yagyu et al. | |

FOREIGN PATENT DOCUMENTS

| | | | |
|---|---|---|---|
| JP | 2001-135278 | A | 5/2001 |
| JP | 2003-036723 | A | 2/2003 |
| JP | 2007-073254 | A | 3/2007 |
| JP | 2010-123276 | A | 6/2010 |
| JP | 2011-193929 | A | 10/2011 |
| JP | 2016-225070 | A | 12/2016 |
| JP | 2017-091916 | A | 5/2017 |
| JP | 2017-123340 | A | 7/2017 |
| JP | 2017-164417 | A | 9/2017 |
| JP | 2018-113116 | A | 7/2018 |
| JP | 2018-190686 | A | 11/2018 |
| WO | 2017/145635 | A1 | 8/2017 |

OTHER PUBLICATIONS

An Office Action; "Notice of Reasons for Refusal", mailed by the Japanese Patent Office dated Jun. 30, 2021, which corresponds to Japanese Patent Application No. 2018-234633 and is related to U.S. Appl. No. 17/312,589; with English language translation.
An Office Action; "Decision of Refusal," mailed by the Japanese Patent Office dated Sep. 7, 2021, which corresponds to Japanese Patent Application No. 2018-234633 and is related to U.S. Appl. No. 17/312,589 with English translation.
Notification of Transmittal of Translation of the International Preliminary Report on Patentability and Translation of Written Opinion of the International Searching Authority; PCT/JP2019/047577; dated Jun. 24, 2021.

\* cited by examiner

ULTRAVIOLET IRRADIATION APPARATUS

TECHNICAL FIELD

The present invention relates to a ultraviolet irradiation apparatus.

BACKGROUND ART

Conventionally, ultraviolet irradiation apparatuses for use in sterilization of goods and skin have been developed (see, for example, Patent Document 1 and Patent Document 2).

PRIOR ART DOCUMENT

Patent Documents

Patent Document 1: JP-A-2018-113116
Patent Document 2: JP-A-2017-164417

SUMMARY OF THE INVENTION

Problems to be Solved by the Invention

FIG. 18 is a diagram schematically showing the structure of a small ultraviolet irradiation apparatus disclosed in Patent Document 2. A ultraviolet irradiation apparatus 100 includes a lamp holder 103 housed in a housing 102 including a gripper 101 and alight irradiation window 104. In the lamp holder 103, an excimer lamp 110 that emits ultraviolet light is housed.

FIG. 19 is a diagram schematically showing the structure of the excimer lamp 110. The excimer lamp 110 includes a cylindrical outer tube 121 and a cylindrical inner tube 122, which is located inside the outer tube 121 and coaxially with the outer tube 121 and has a smaller inner diameter than the outer tube 121. The outer tube 121 and the inner tube 122 are sealed at their ends in a direction d1 to form an annular light-emitting space between them and a discharge gas 123G is filled in the space.

A net- or mesh-shaped outer electrode 124 is provided on the outer wall surface of the outer tube 121, and a film-shaped inner electrode 125 is provided on the inner wall surface of the inner tube 122. Both the outer electrode 124 and the inner electrode 125 are electrically connected to a power supply part 126 that is capable of generating a high-frequency AC voltage.

When the power supply part 126 applies a high-frequency AC voltage between the outer electrode 124 and the inner electrode 125, a voltage is applied to the discharge gas 123G through the tubular bodies of the outer tube 121 and the inner tube 122 so that a discharge plasma is generated in a discharge space filled with the discharge gas 123G. As a result, atoms of the discharge gas 123G are excited into the excimer state, and excimer emission occurs when the atoms shift to the ground state.

The wavelength of excimer emission can be changed depending on the type of gas used as the discharge gas 123G. For example, Patent Document 1 discloses that ultraviolet light having a main emission wavelength of 222 nm suitable for sterilization can be obtained by using krypton chloride (KrCl) gas as the discharge gas 123G.

Meanwhile, in the excimer lamp 110 shown in FIG. 19, as described above, two types of tubular bodies (121, 122) coaxially arranged. Therefore, the housing 102 that houses the excimer lamp 110 needs to have a certain size. The ultraviolet irradiation apparatus 100 disclosed in Patent Document 2 is intended to be used for treatment of skin diseases, and therefore its user and usage situation are limited. However, the excimer lamp 110 having such a structure as shown in FIG. 19 is too large for ultraviolet irradiation apparatuses more widely used for general purposes such as sterilization and deodorization. For example, it is practically difficult to use the ultraviolet irradiation apparatus 100 shown in FIG. 19 to sterilize or deodorize shoes.

In view of the above problem, it is an objective of the present invention to provide a ultraviolet irradiation apparatus significantly downsized compared to a conventional structure.

Means for Solving the Problems

The present invention is directed to a ultraviolet irradiation apparatus including:

a first electrode block and a second electrode block located apart from each other in a first direction or located in an electrically-insulated state in the first direction;

a recessed groove formed on a side surface of each of the first electrode block and the second electrode block so as to extend in the first direction;

a first discharge lamp including an excimer lamp, partially fitted into the recessed grooves formed in both the first electrode block and the second electrode block, and located across the first electrode block and the second electrode block so as to extend in the first direction;

a power supply part for supplying electrical power to the first discharge lamp;

a first current-carrying member that electrically connects the first electrode block and the power supply part;

a second current-carrying member capable of electrically connecting the second electrode block and the power supply part at an electrical potential different from that of the first current-carrying member; and a light irradiation window for extracting ultraviolet light emitted from the first discharge lamp to outside, the light irradiation window being formed in a side of the first discharge lamp opposite from the first electrode block and in a side of the first discharge lamp opposite from the second electrode block.

In the above structure, the first discharge lamp is partially fitted into the recessed grooves formed in both the first electrode block and the second electrode block, and is located across both the first electrode block and the second electrode block. Thus, the first discharge lamp can have a simple straight tube structure for electrical discharge, and does not need to adopt a conventional double tube structure. For example, the tubular body of the first discharge lamp has a length in the first direction of 15 mm to 200 mm and an outer diameter of 2 mm to 16 mm.

Specifically, a contact region between the recessed groove formed in the first electrode block and the first discharge lamp (more specifically, the tubular body of the first discharge lamp) forms one of electrodes (hereinafter referred to as a "first electrode region"), and a contact region between the recessed groove formed in the second electrode block and the first discharge lamp (more specifically, the tubular body of the first discharge lamp) forms the other electrode (hereinafter referred to as a "second electrode region"). The first electrode block and the second electrode block are located apart from each other in the first direction or located in an electrically-insulated state in the first direction, and therefore do not cause a short circuit. Further, such a structure allows the first electrode region and the second electrode region to be formed at positions apart from each other in the first direction on the side surface of the tubular body of the first discharge lamp.

In other words, the structure described above causes a potential difference between an electrical potential applied to the first electrode block from the power supply part through the first current-carrying member and an electrical potential applied to the second electrode block from the power supply part through the second current-carrying member, so that a voltage is applied between the first electrode region and the second electrode region of the first discharge lamp which are apart from each other in the first direction. This causes electrical discharge in the first discharge lamp to emit ultraviolet light.

The light irradiation window is formed in a side of the first discharge lamp opposite from the first electrode block and in a side of the first discharge lamp opposite from the second electrode block. Therefore, ultraviolet light emitted from the first discharge lamp is extracted to the outside of the apparatus from the side not blocked by the first electrode block and the second electrode block.

Each of the first electrode block and the second electrode block may be made of a conductive material as a whole.

As an alternative example, the first electrode block may be entirely made of an insulating member, while conductive sheet members are formed in a region to which the first current-carrying member is connected (hereinafter referred to as a "first specific region") and the first electrode region. In this case, the conductive sheet members may be connected, for example, so that the first specific region and the first electrode region are electrically connected.

Similarly, the second electrode block may be entirely made of an insulating member, while conductive sheet members are formed in a region to which the second current-carrying member is connected (hereinafter referred to as a "second specific region") and the second electrode region. In this case, the conductive sheet members may be connected, for example, so that the second specific region and the second electrode region are electrically connected.

The first electrode block and the second electrode block may be made of a metallic member having reflective properties for the light emitted from the discharge lamp.

Such a structure makes it possible to return ultraviolet light emitted from the first discharge lamp, which is travelling toward the first electrode block and second electrode block sides, to the light irradiation window side, improving light extraction to the outside.

The first current-carrying member may include a first screw member inserted at a predetermined position into the first electrode block and a first wire connecting the first screw member to the power supply part, and the second current-carrying member may include a second screw member inserted at a predetermined position into the second electrode block and a second wire connecting the second screw member to the power supply part.

Particularly, the first discharge lamp is located across the electrode blocks in a state where it is fitted into the recessed groove formed in each of the electrode blocks. As described above, the contact region between the first discharge lamp and the recessed groove formed in each of the electrode blocks constitutes the electrode region (first electrode region, and second electrode region) for generating electrical discharge. Therefore, it is preferred that the first discharge lamp and each of the electrode blocks are stably held in a contact state. From such a viewpoint, the ultraviolet irradiation apparatus preferably has a holding member provided for each of the electrode blocks to press the first discharge lamp against each of the electrode blocks from the opposite side from each of the electrode blocks.

The holding member partially includes a lamp presser having a curved shape so as to be laid along a part of the external surface of tubular body of the first discharge lamp. Further, the holding member is preferably threadably mounted on each of the electrode blocks in a position different from the lamp presser to allow the lamp presser to sufficiently fulfill the function of pressing the first discharge lamp against each of the electrode blocks.

More specifically, each of the electrode blocks is preferably threadably mounted on the first discharge lamp via the holding member, and in this case, each of the electrode blocks is previously subjected to thread cutting. That is, the first electrode block should have a screw thread for engaging a first screw member as the first current-carrying member which is additionally formed in a position different from the position of a screw thread for threadably mounting the holding member thereon. Similarly, the second electrode block should have a screw thread for engaging a second screw member as the second current-carrying member which is additionally formed in a position different from the position of a screw thread for threadably mounting the holding member thereon. Such a structure makes it possible to simply establish an electrical connection between the power supply part and each of the electrode blocks without complicating a production process.

Each of the first electrode block and the second electrode block may have the recessed grooves formed in two or more positions apart from each other when viewed from the first direction, and a number of the first discharge lamps of the ultraviolet irradiation apparatus may correspond to a number of the recessed grooves formed in each of the first electrode block and the second electrode block.

Such a structure makes it possible to achieve a ultraviolet irradiation apparatus that emits ultraviolet light of a higher irradiance while preventing an increase in the scale of the apparatus.

The ultraviolet irradiation apparatus may include a second discharge lamp having a lower starting voltage than the first discharge lamp, wherein each of the first electrode block and the second electrode block has the recessed grooves formed in two or more positions apart from each other when viewed from the first direction, and a number of the recessed grooves formed in each of the first electrode block and the second electrode block corresponds to a sum of a number of the first discharge lamps and a number of the second discharge lamps.

In order to achieve a high-power output of the first discharge lamp, it is necessary to increase the pressure of a gas filled therein, which results in an increase in a discharge starting voltage. Further, also when a gas filled in the first discharge lamp contains a halogen gas, a discharge starting voltage increases. Such a structure as described above makes it possible to reduce the time before the starting of the first discharge lamp because the second discharge lamp having a lower starting voltage than the first discharge lamp is provided. Further, similarly to the first discharge lamp, electrical power can be supplied also to the second discharge lamp through the electrode blocks, which makes it possible to prevent an increase in the scale of the apparatus.

The second discharge lamp is constituted from, for example, an external electrode-type discharge lamp.

In this case, the number of the first discharge lamps may be equal to or larger than the number of the second discharge lamps.

The first discharge lamp may include a tubular body filled with a first discharge gas capable of emitting ultraviolet light, and the second discharge lamp may include a tubular body filled with a second discharge gas capable of emitting visible light.

When the first discharge lamp is turned on, ultraviolet light is emitted through the light irradiation window. However, ultraviolet light has a shorter wavelength than visible light, and is therefore difficult to be visually recognized. Therefore, there is possibility that ultraviolet light may be accidentally irradiated to a non-target object near the light irradiation window under the mistaken impression that the first discharge lamp is not lit, even though it is actually lit.

In such a structure as described above, the second discharge lamp can function as both a light source as a starting assistance as well as a light source for lighting confirmation for visually confirming that the first discharge lamp is lit. This makes it possible to achieve a ultraviolet irradiation apparatus including a lighting confirmation light source while preventing an increase in the scale of the apparatus.

The first discharge gas may contain Kr and Cl, and the second discharge gas may contain Ne.

When the first discharge gas contains Kr and Cl, the first discharge lamp generates ultraviolet light having a main emission wavelength of 222 nm. Ultraviolet light having a wavelength of 230 nm or less is absorbed by the stratum corneum of the skin and does not reach epidermal cells, so even if such ultraviolet light is irradiated to a human body, the influence on the cells of the human body is suppressed. For this reason, general consumers can use the ultraviolet irradiation apparatus for, for example, sterilization/deodorization of daily necessities.

The power supply part may include a battery and an electrical component that transforms a voltage supplied from the battery, and the ultraviolet irradiation apparatus may include:

a battery holder that houses the battery, an electrical component holder that is located in a position apart from the battery holder and houses the electrical component:

a lamp holder that is located in a position apart from the battery holder and the electrical component holder, houses the first electrode block, the second electrode block, and the first discharge lamp, and has the light irradiation window formed in part thereof; and a casing member that houses the battery holder, the electrical component holder, and the lamp holder.

Such a structure makes it possible to achieve, for example, a portable ultraviolet irradiation apparatus.

Effect of the Invention

According to the present invention, it is possible to provide a ultraviolet irradiation apparatus significantly downsized compared to a conventional structure.

MODE FOR CARRYING OUT THE INVENTION

The structure of an embodiment of a ultraviolet irradiation apparatus according to the present invention will be described with reference to the drawings of FIG. 1 to FIG. 15. It is to be noted that all the following drawings are schematically shown, and the dimensional ratios of the drawings are not necessarily consistent with actual dimensional ratios. Further, the dimensional ratios of the drawings are not necessarily consistent with each other.

Figure 1:
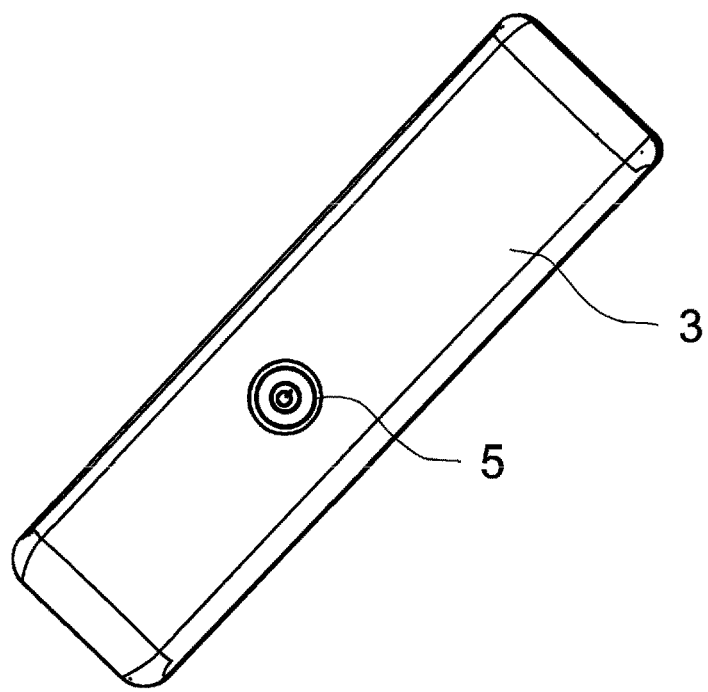
FIG. 1 is a perspective view schematically showing the structure of an embodiment of a ultraviolet irradiation apparatus according to the present invention.
Figure 1:
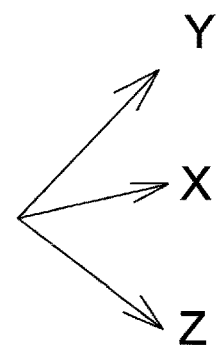
Figure 2:
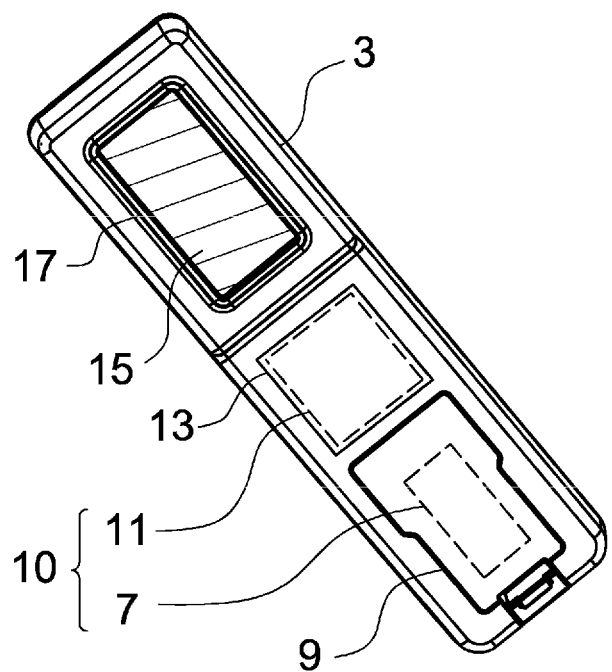
FIG. 2 is a perspective view schematically showing the structure of the embodiment of the ultraviolet irradiation apparatus according to the present invention.
Figure 2:
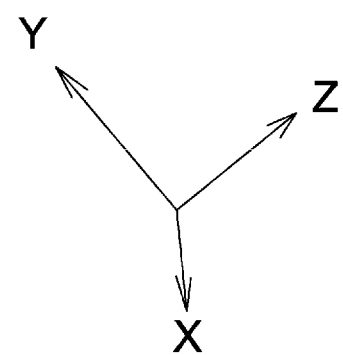

FIG. 1 and FIG. 2 are perspective views schematically showing the structure of an embodiment of a ultraviolet irradiation apparatus according to the present invention. It is to be noted that the following description with reference to the drawings will be made using an XYZ coordinate system in which a direction in which ultraviolet light is extracted is defined as an X direction and two directions orthogonal to the X direction are defined as a Y direction and a Z direction. It is to be noted that in this embodiment, the Y direction corresponds to a "first direction".

A ultraviolet irradiation apparatus 1 includes a casing member 3. The casing member 3 houses a battery holder 9, an electrical component holder 13, and a lamp holder 17 therein. The lamp holder 17 houses discharge lamps (21, 22) that will be described later with reference to FIG. 3 etc. The battery holder 9 houses a battery 7. The electrical component holder 13 houses an electrical component 11 including a transformer for transforming a voltage supplied from the battery 7. A voltage transformed by the electrical component 11 is supplied to the discharge lamps (21, 22) so that the discharge lamps (21, 22) are turned on. In this embodiment, the battery 7 and the electrical component 11 constitute a power supply part 10. In this embodiment, the electrical component holder 13 is located in the +Y direction with respect to the battery holder 9, and the lamp holder 17 is located in the +Y direction with respect to the electrical component holder 13.

For example, as shown in FIG. 1, a power button 5 is located on a part of the surface of the casing member 3. When the power button 5 is operated, an electrical connection is formed between the power supply part 10 and the discharge lamps (21, 22) so that the discharge lamps (21, 22) start to light up.

As shown in FIG. 2, a light irradiation window 15 for extracting ultraviolet light is formed in part of the casing member 3. The light irradiation window 15 is made of a material that transmits ultraviolet light, such as quartz glass.

It is to be noted that this embodiment will be described with reference to a case where ultraviolet light is extracted in the +X direction. Therefore, the light irradiation window 15 is provided only on one YZ plane side of the casing member 3. However, the direction in which ultraviolet light is extracted is not limited to one direction, and the present invention does not exclude a structure in which ultraviolet light is extracted in two or more directions. Such a structure will be described later in the section of other embodiments.

Figure 3:
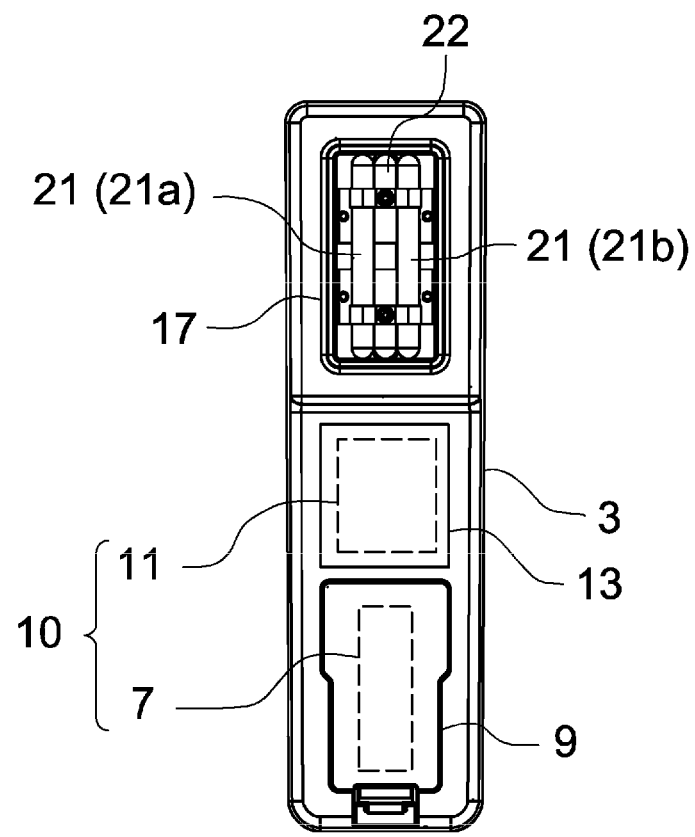
FIG. 3 is a plan view schematically showing the structure of the embodiment of the ultraviolet irradiation apparatus according to the present invention, w % herein some components are not shown.
Figure 3:
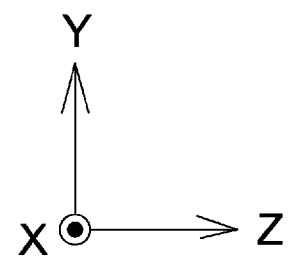

FIG. 3 is a schematic plan view of the ultraviolet irradiation apparatus 1 viewed from the +X direction, wherein the light irradiation window 15 is not shown for convenience of explanation. In this embodiment, the lamp holder 17 houses the discharge lamps 21 that emit ultraviolet light (hereinafter referred to as a "first discharge lamp 21") and the discharge lamp 22 that emits visible light (hereinafter referred to as a "second discharge lamp 22) therein.

For example, the ultraviolet irradiation apparatus 1 according to this embodiment includes two first discharge lamps 21 and one second discharge lamp 22. In this embodiment, the two first discharge lamps 21 are located next to each other in the Z direction. When it is necessary to distinguish between the two first discharge lamps 21 in the following description, there is a case where the first discharge lamp 21 located on the −Z side is referred to as a "first discharge lamp 21a" and the first discharge lamp 21 located on the +Z side is referred to as a "first discharge lamp 21b".

Both the first discharge lamp 21 and the second discharge lamp 22 are configured to discharge and emit light when supplied with electrical power from the power supply part 10.

Figure 4:
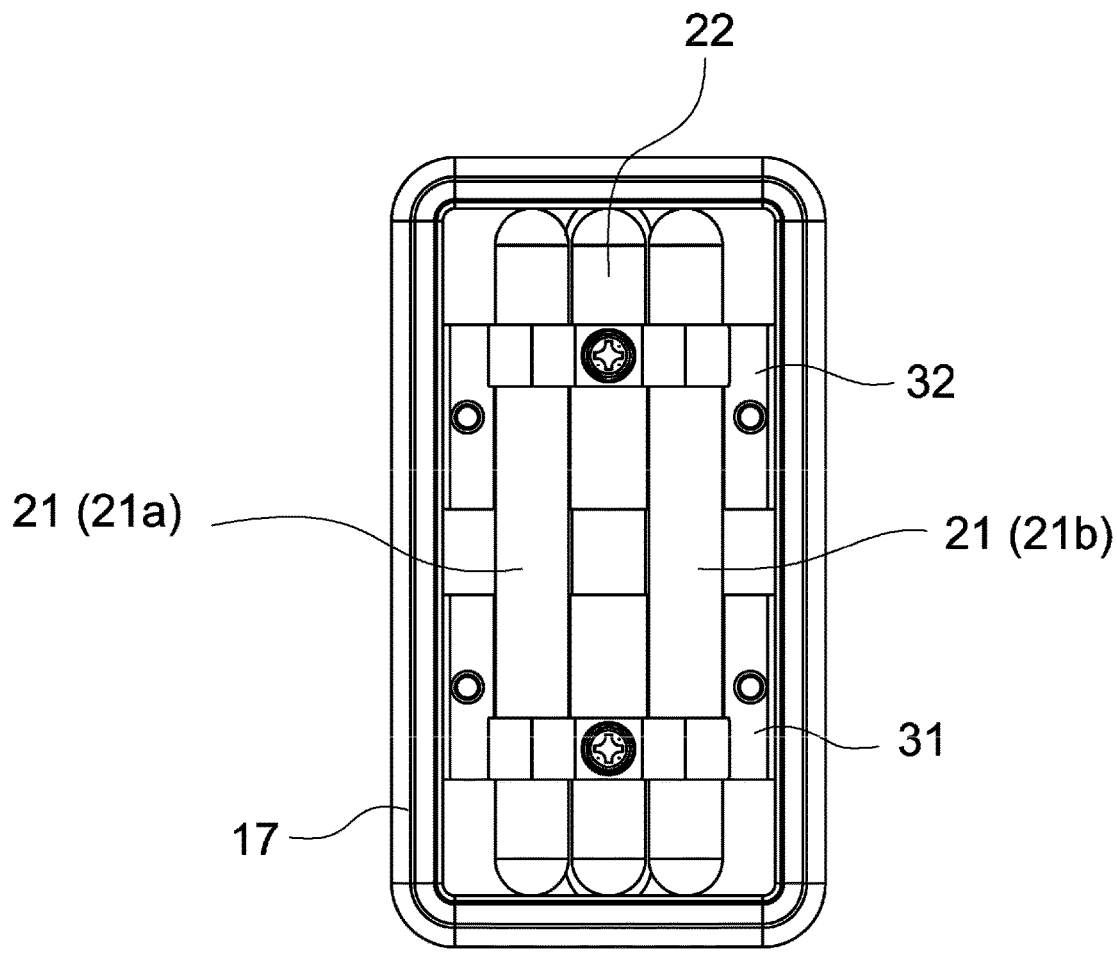
FIG. 4 is a partially enlarged view of FIG. 3.
Figure 4:
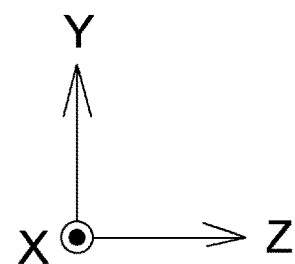

FIG. 4 is an enlarged view of the discharge lamps (21, 22) and their vicinity shown in FIG. 3. The ultraviolet irradiation apparatus 1 according to this embodiment includes two electrode blocks (31, 32) located apart from each other in the Y direction. Both the discharge lamps (21, 22) are located across the two electrode blocks (31, 32) so as to come in contact with the two electrode blocks (31, 32). The positional relationship between the electrode blocks (31, 32) and the discharge lamps (21, 22) will be described with reference to FIG. 5 and FIG. 6. It is to be noted that in the following description, the electrode block 31 is sometimes referred to as a "first electrode block 31", and the electrode block 32 is sometimes referred to as a "second electrode block 32".

Figure 5:
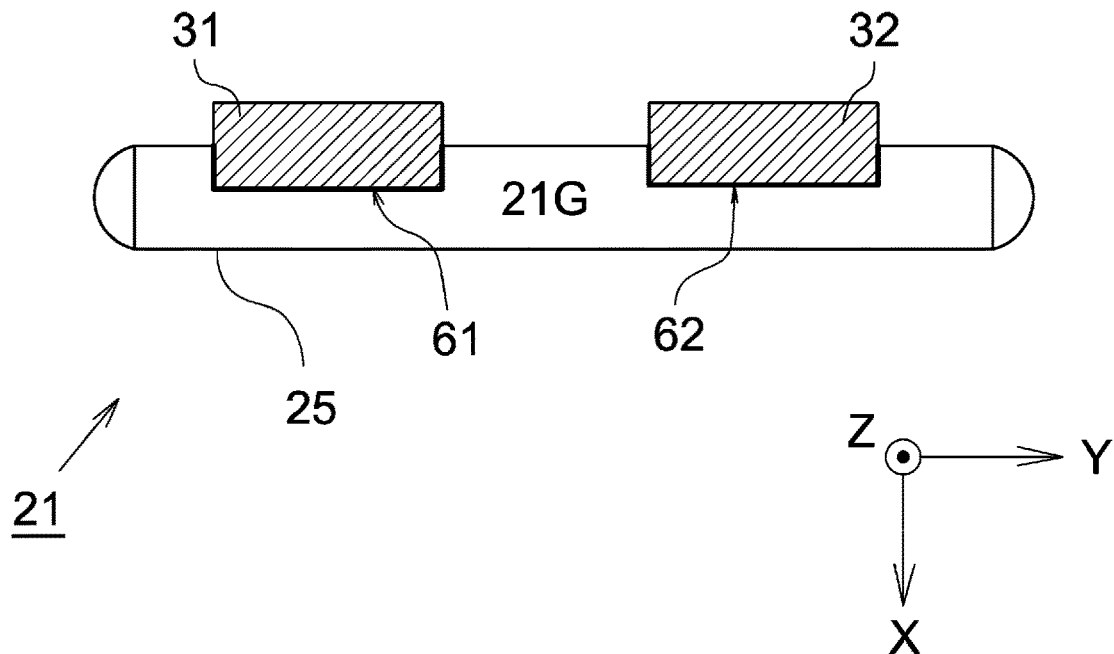
FIG. 5 is a diagram schematically showing the positional relationship between a first discharge lamp and electrode blocks.
Figure 6:
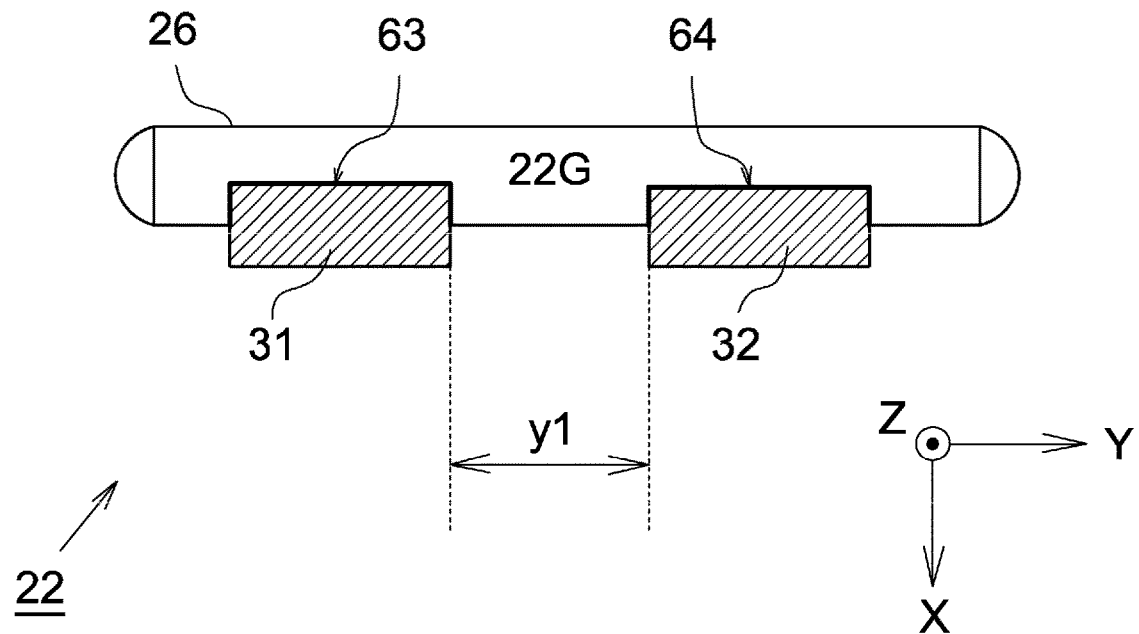
FIG. 6 is a diagram schematically showing the positional relationship between a second discharge lamp and the electrode blocks.

FIG. 5 is a diagram schematically showing the positional relationship between the first discharge lamp 21 and the electrode blocks (31, 32). FIG. 6 is a diagram schematically showing the positional relationship between the second discharge lamp 22 and the electrode blocks (31, 32).

As will be described later, a recessed groove is formed in each of the electrode blocks (31, 32) so as to extend in the Y direction. The first discharge lamp 21 includes a tubular body 25 filled with a first discharge gas 21G (hereinafter referred to as a "first tubular body 25"). The first tubular body 25 is fitted into the recessed groove formed in each of the electrode blocks (31, 32) so as to be in contact with part of the electrode blocks (31, 32). When a voltage is applied between a first electrode region 61, which is constituted from a contact area between the first tubular body 25 and the first electrode block 31, and a second electrode region 62, which is constituted from a contact area between the first tubular body 25 and the second electrode block 32, light emission occurs in the first tubular body 25 due to the excimer discharge of the first discharge gas 21G. That is, the first discharge lamp 21 is constituted from an excimer lamp.

The first discharge gas 21G is made of a material that can emit ultraviolet light by electrical discharge. The first discharge gas 21G contains, for example, a noble gas such as xenon (Xe), argon (Ar), neon (Ne), krypton (Kr) or a mixed gas of two or more of them and a halogen gas such as fluorine (F), chlorine (Cl), or bromine (Br) or a mixed gas of two or more of them. For example, the first discharge gas 21G is made of a mixed gas containing Kr and Cl. In this case, the first discharge lamp 21 emits ultraviolet light having a main wavelength of 222 nm.

In this embodiment, the electrode blocks (31, 32) are made of a metallic material, and are preferably made of a material having reflective properties for the light emitted from the first discharge lamp 21. For example, the electrode blocks (31, 32) are made of Al or stainless steel.

As described above, the ultraviolet irradiation apparatus 1 according to this embodiment is configured so that ultraviolet light is extracted in the +X direction through the light irradiation window 15. Therefore, in this embodiment, the electrode blocks (31, 32) are located on the −X side of the first tubular body 25 from the viewpoint of enhancing the extraction efficiency of ultraviolet light. However, when the electrode blocks (31, 32) are made of a material having the reflective properties for ultraviolet light as described above, ultraviolet light emitted from the first tubular body 25 and travelling in the −X direction is also allowed to travel in the +X direction by reflection from the electrode blocks (31, 32).

The second discharge lamp 22 includes a tubular body 26 filled with a second discharge gas 22G (hereinafter referred to as a "second tubular body 26"). As will be described later, when viewed in the Y direction, each of the electrode blocks (31, 32) has recessed grooves formed in positions apart from each other. The second tubular body 26 is fitted into one of the recessed grooves formed in each of the electrode blocks (31, 32), which is different from the recessed groove into which the first tubular body 25 is fitted, so as to be in contact with part of the electrode blocks (31, 32). When a voltage is applied between a third electrode region 63, which is constituted from a contact area between the second tubular body 26 and the first electrode block 31, and a fourth electrode region 64, which is constituted from a contact area between the second tubular body 26 and the second electrode block 32, light emission occurs in the second tubular body 26 due to the electrical discharge of the second discharge gas 22G. That is, the second discharge lamp 22 is constituted from an external electrode-type discharge lamp.

The second discharge gas 22G is made of a material that can emit visible light by electrical discharge. The second discharge gas 22G contains, for example, a noble gas such as Ne, Ar, Kr, or Xe. For example, the second discharge gas 22G is made of Ne. In this case, the second discharge lamp 22 emits visible light having a main wavelength of 500 to 800 nm. It is to be noted that the gas type and charged pressure of the second discharge gas 22G are set so that the discharge starting voltage of the second discharge lamp 22 is lower than that of the first discharge lamp 21.

In the ultraviolet irradiation apparatus 1 according to this embodiment, the electrode blocks (31, 32) are located on the +X side of the second tubular body 26. However, in the ultraviolet irradiation apparatus 1 according to this embodiment, the first electrode block 31 and the second electrode block 32 are located apart from each other in the Y direction (having gap y1). Therefore, visible light emitted in the second tubular body 26 can also travel in the +X direction through the gap y1 and can be extracted through the light irradiation window 15.

The positional relationship between each of the electrode blocks (31, 32) and each of the discharge lamps (21, 22) will be described in detail with reference to FIG. 7 to FIG. 15.

Figure 7:
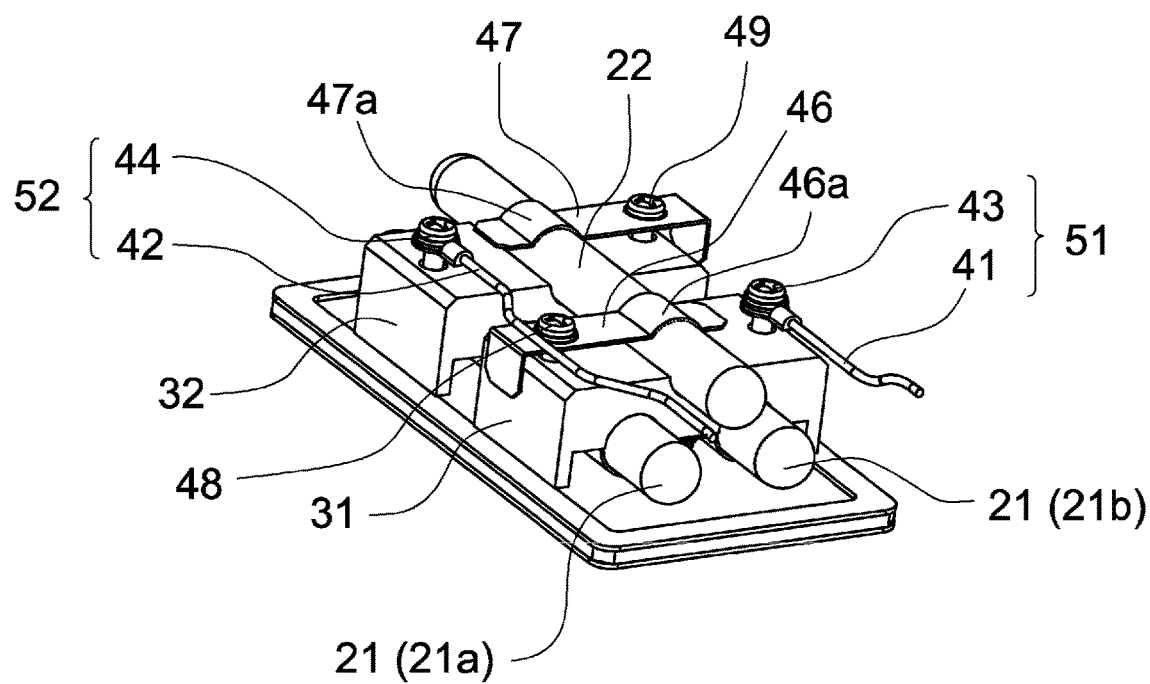
FIG. 7 is a schematic perspective view showing components near the electrode blocks and the discharge lamps extracted from the ultraviolet irradiation apparatus according to the present invention.
Figure 7:
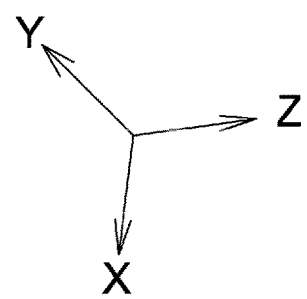
Figure 8:
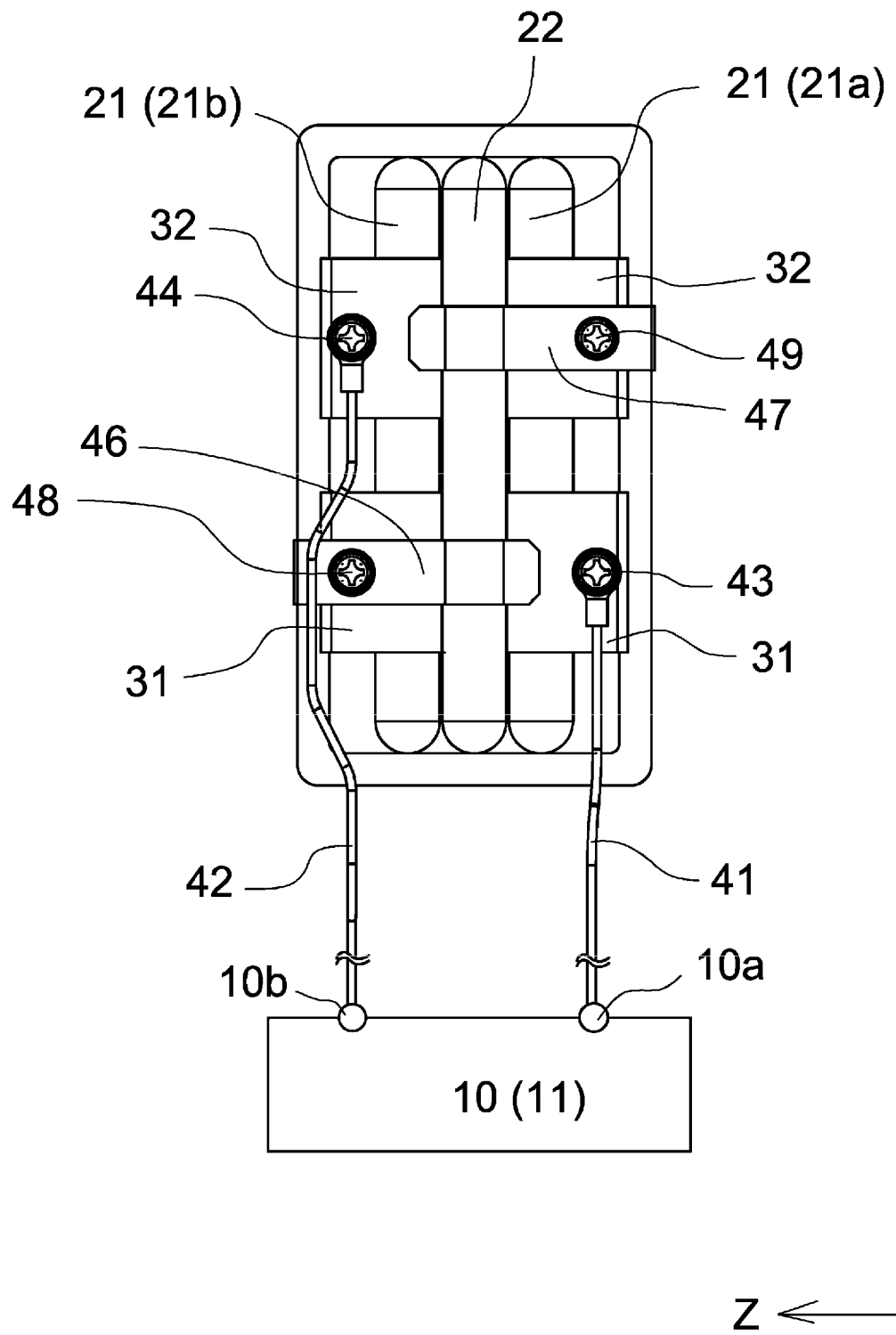
FIG. 8 is a schematic plan view of FIG. 7 as viewed from a −X direction.

FIG. 7 is a schematic perspective view showing the electrode blocks (31, 32), the discharge lamps (21, 22), and components around them extracted from the ultraviolet irradiation apparatus 1. FIG. 8 is a schematic plan view of the components shown in FIG. 7 viewed from the −X direction. In FIG. 8, the electrical component 11 (power supply part 10) is also schematically shown for the convenience of explanation. In contrast to FIG. 8, FIG. 9 is a schematic plan view of the components shown in FIG. 7 viewed from the +X direction.

Figure 10:
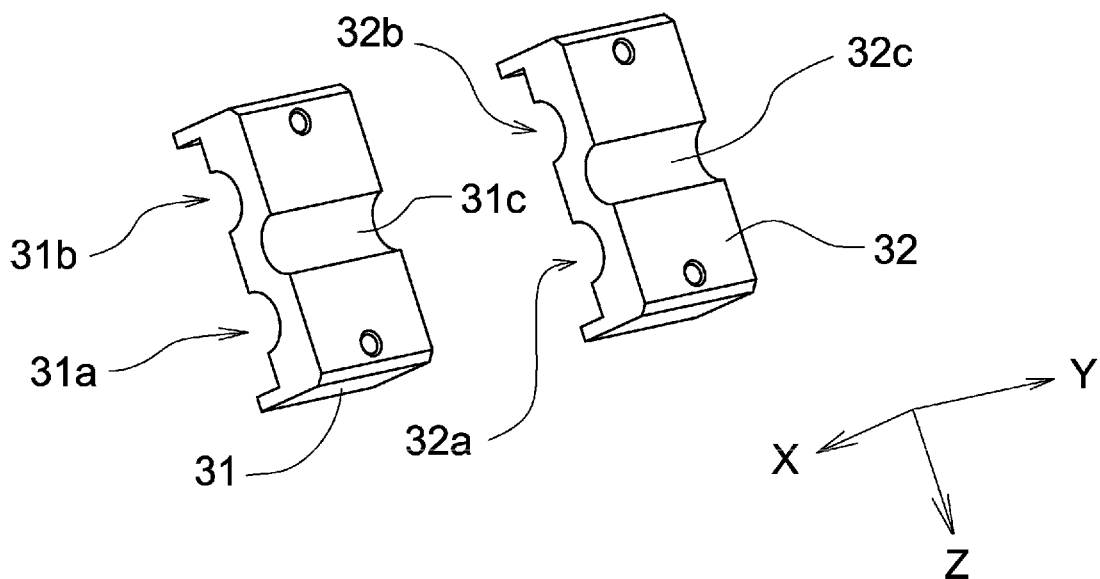
FIG. 10 is a schematic perspective view of the electrode blocks.
Figure 11:
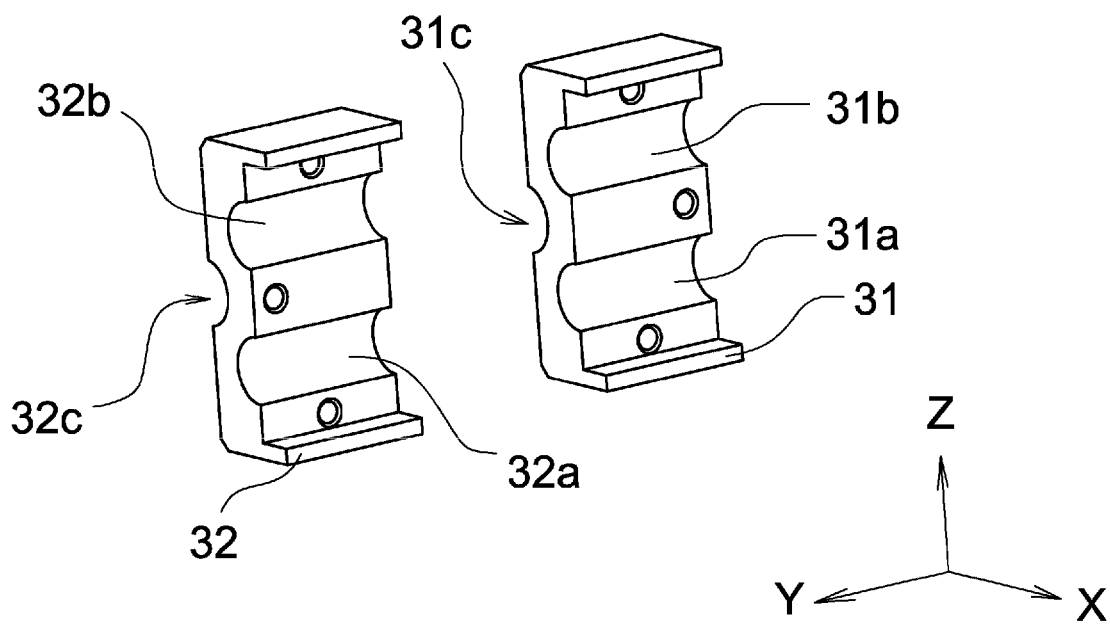
FIG. 11 is a schematic perspective view of the electrode blocks, which is different from FIG. 10 in direction from which the electrode blocks are viewed.

FIG. 10 and FIG. 11 are both perspective views schematically showing the extracted electrode blocks (31, 32). For the convenience of diagrammatic representation, two diagrams shown in FIG. 10 and FIG. 11 are different in direction from which the electrode blocks (31, 32) are viewed.

Figure 12:
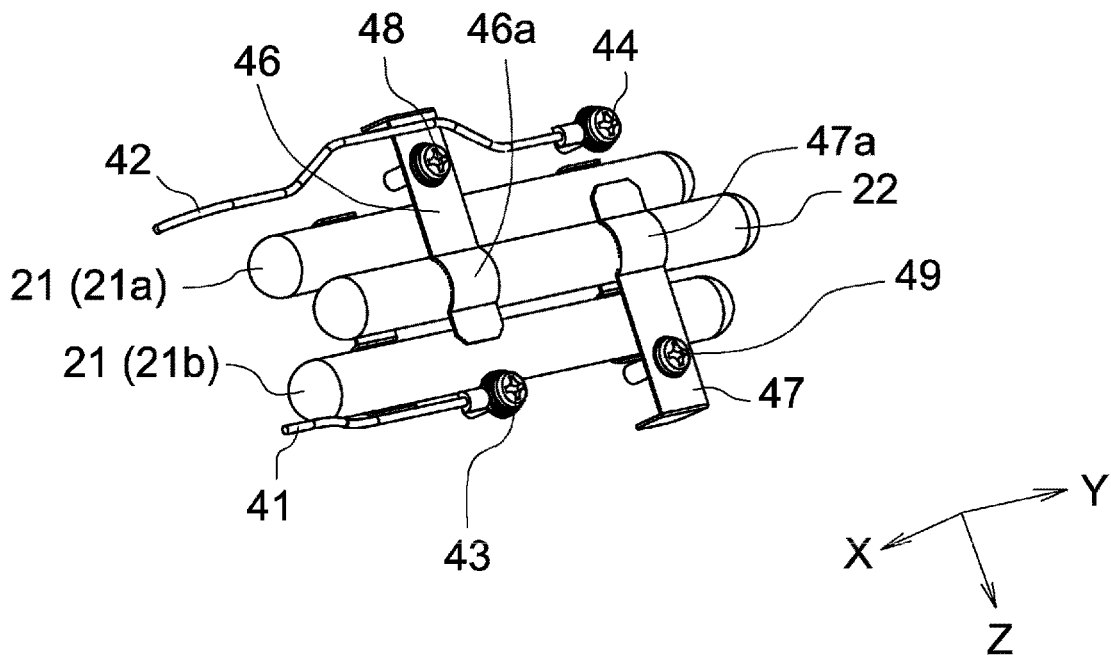
FIG. 12 is a perspective view schematically showing the relation of connection of the discharge lamps, wherein the electrode blocks are not shown.
Figure 13:
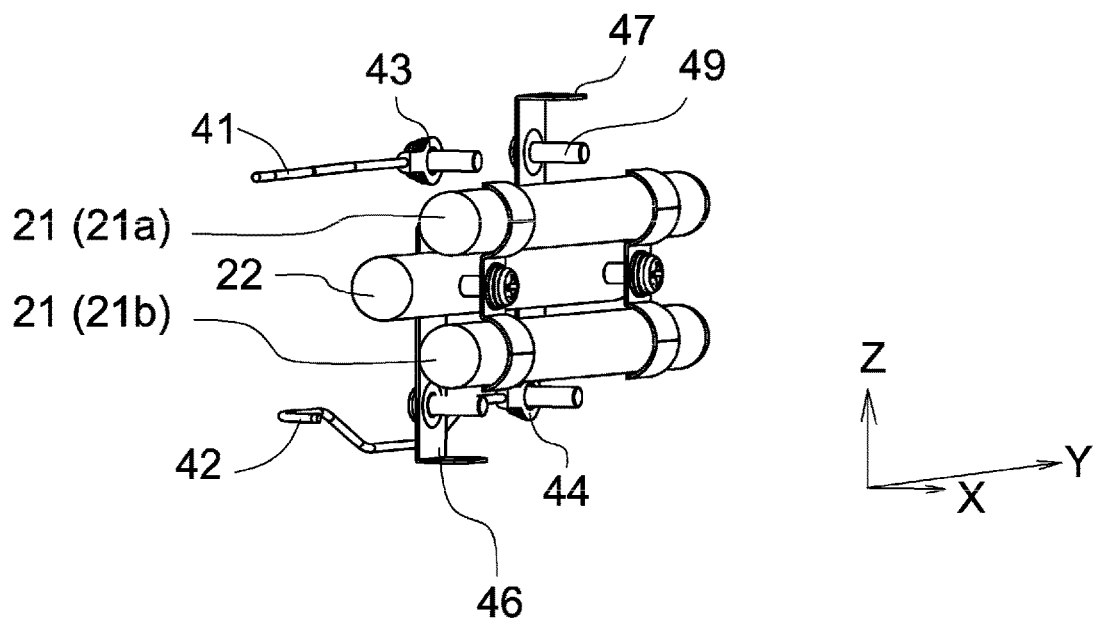
FIG. 13 is a perspective view schematically showing the relation of connection of the discharge lamps which is different from FIG. 12 in direction from which the discharge lamps are viewed, wherein the electrode blocks are not shown.

FIG. 12 and FIG. 13 are perspective views schematically showing the relation of connection of the discharge lamps (21, 22), wherein the electrode blocks (31, 32) are not shown. For the convenience of diagrammatic representation, two diagrams shown in FIG. 12 and FIG. 13 are different in direction from which the discharge lamps (21, 22) are viewed.

Figure 9:
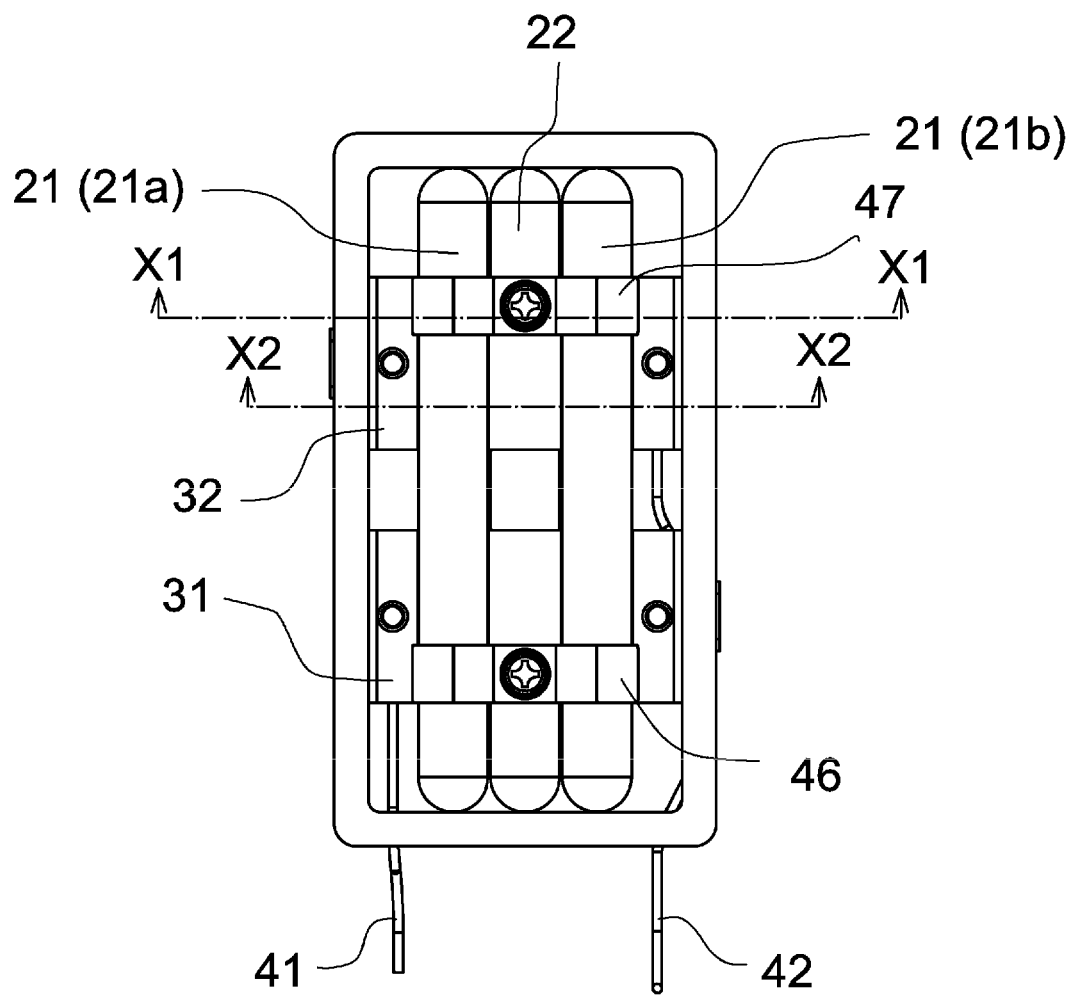
FIG. 9 is a schematic plan view of FIG. 7 as viewed from a +X direction.
Figure 9:
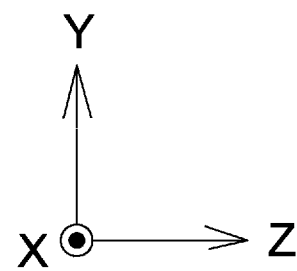
Figure 14:
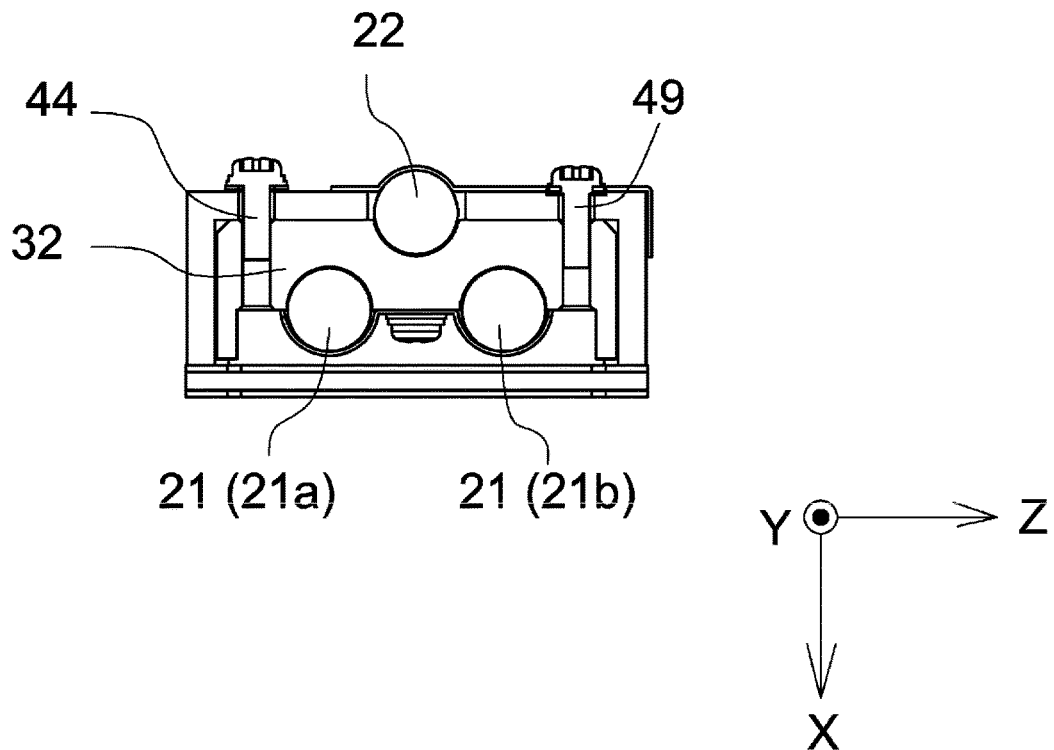
FIG. 14 is a schematic sectional view taken along an X1-X1 line shown in FIG. 9.
Figure 15:
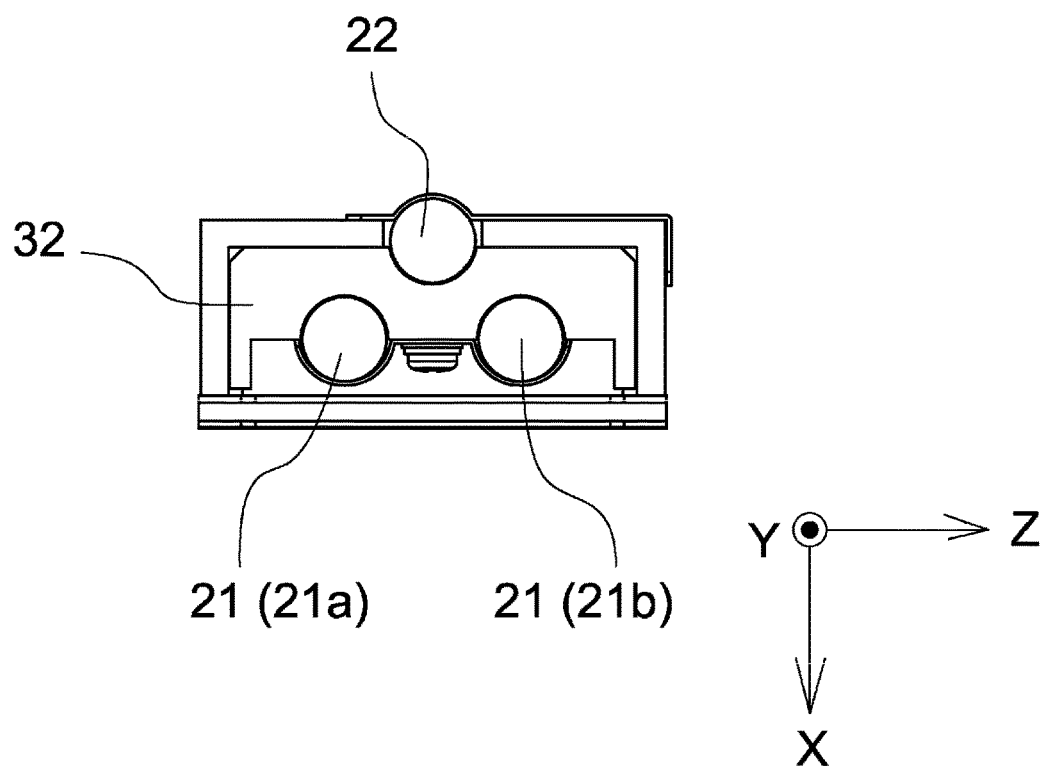
FIG. 15 is a schematic sectional view taken along an X2-X2 line shown in FIG. 9.

FIG. 14 is a schematic sectional view taken along a line X1-X1 shown in FIG. 9. FIG. 15 is a schematic sectional view taken along a line X2-X2 shown in FIG. 9. It is to be noted that, in both FIG. 14 and FIG. 15, the second discharge lamp 22 is located on the upper side in the plane of paper from the convenience of diagrammatic representation.

As shown in FIG. 10 and FIG. 11, the first electrode block 31 has recessed grooves (31a, 31b, 31c) formed in different positions on its side surfaces extending in the Y direction. Similarly, the second electrode block 32 has recessed grooves (32a, 32b, 32c) formed in different positions on its side surfaces extending in the Y direction. These recessed grooves (31a, 31b, 31c, 32a, 32b. 32c) each have a shape fitted to the shape of side surface of the tubular body (25, 26) of the discharge lamp (21, 22) and are configured so that part of the tubular body (25, 26) of the discharge lamp (21, 22) can be fitted therein.

More specifically, the tubular body 25 (first tubular body 25) of the first discharge lamp 21a is fitted into the recessed groove 31a and the recessed groove 32a, the tubular body 25 (first tubular body 25) of the first discharge lamp 21b is fitted into the recessed groove 31b and the recessed groove 32b, and the tubular body 26 (second tubular body 26) of the second discharge lamp 22 is fitted into the recessed groove 31c and the recessed groove 32c.

Hereinafter, the recessed grooves (31a. 31b) for the first discharge lamp 21 formed in the first electrode block 31 are sometimes referred to as "first recessed grooves (31a, 31b), and the recessed groove 31c for the second discharge lamp 22 formed in the first electrode block 31 is sometimes referred to as a "second recessed groove 31c". Similarly, the recessed grooves (32a. 32b) for the first discharge lamp 21 formed in the second electrode block 32 are sometimes referred to as "third recessed grooves (32a, 32b), and the recessed groove 32c for the second discharge lamp 22 formed in the second electrode block 32 is sometimes referred to as a "fourth recessed groove 32c".

In the first electrode block 31, the first recessed grooves (31a, 31b) are formed in the +X-side side surface thereof, and the second recessed groove 31c is formed in the −X-side side surface opposite thereto. Similarly, in the second electrode block 32, the third recessed grooves (32a. 32b) are formed in the +X-side side surface thereof, and the fourth recessed groove 32c is formed in the −X-side side surface opposite thereto.

As described above, the tubular body 25 of the first discharge lamp 21a is located across both the electrode blocks (31, 32) while fitted into the first recessed groove 31a and the third recessed groove 32a. As described above, the electrode blocks (31, 32) are made of metallic members, and therefore the first electrode region 61 is formed in a contact area between the first recessed groove 31a of the first electrode block 31 and the tubular body 25 of the first discharge lamp 21a. The first electrode block 31 and the second electrode block 32 are located in positions apart from each other in the Y direction, and therefore the second electrode region 62 electrically separated from the first electrode region 61 is formed in a contact area between the third recessed groove 32a of the second electrode block 32 and the first tubular body 25 of the first discharge lamp 21a. The same is true for the first discharge lamp 21b.

Similarly, the tubular body 26 of the second discharge lamp 22 is located across both the electrode blocks (31, 32) while fitted into the second recessed groove 31c and the fourth recessed groove 32c. As described above, the electrode blocks (31, 32) are made of metallic members, and therefore the third electrode region 63 is formed in a contact area between the second recessed groove 31c of the first electrode block 31 and the tubular body 26 of the second discharge lamp 22. The first electrode block 31 and second electrode block 32 are located in positions apart from each other in the Y direction, and therefore the fourth electrode region 64 electrically separated from the third electrode region 63 is formed in a contact area between the fourth recessed groove 32c of the second electrode block 32 and the second tubular body 26 of the second discharge lamp 22.

As shown in FIG. 8, the power supply part 10 (more specifically, the electrical component 11) includes a first terminal 10a and a second terminal 10b. The first terminal 10a is electrically connected to the first electrode block 31 through a first wire 41 and a first screw member 43. Similarly, the second terminal 10b is electrically connected to the second electrode block 32 through a second wire 42 and a second screw member 44. That is, in this embodiment, as shown in FIG. 7, a first current-carrying member 51 is formed from the first wire 41 and the first screw member 43, and a second current-carrying member 52 is formed from the second wire 42 and the second screw member 44.

Both the first screw member 43 and the second screw member 44 are made of a conductive metallic material. The first screw member 43 is joined to the first wire 41 and inserted into the first electrode block 31. The second screw member 44 is joined to the second wire 42 and inserted into the second electrode block 32. A sectional view of FIG. 14 shows a structure in which an electrical current is applied to the second electrode block 32 through the second screw member 44. It is to be noted that, for comparison, a sectional view of FIG. 15 shows a portion where the second screw member 44 is not provided.

The ultraviolet irradiation apparatus 1 shown in FIG. 7 by way of example includes a holding member 46 for holding the first electrode block 31 and the discharge lamps (21, 22) in a contact state. The holding member 46 partially has a presser member 46a having a shape fitted to the shape of external surface of the discharge lamp (21, 22). The holding member 46 is threadably mounted on the first electrode block 31 via a fixation screw 48. Similarly, the ultraviolet irradiation apparatus 1 includes a holding member 47 for holding the second electrode block 32 and the discharge lamps (21, 22) in a contact state. The holding member 47 partially has a presser member 47a having a shape fitted to the shape of external surface of the discharge lamp (21, 22). The holding member 47 is threadably mounted on the second electrode block 32 by a fixation screw 49.

Such a structure as described above makes it possible to apply a voltage to the discharge lamps (21, 22) through the electrode regions (61, 62, 63, 64) formed from the contact regions with the recessed grooves (31a, 31b, 31c, 32a, 32b, 32c) formed in the electrode blocks (31, 32). Therefore, the discharge lamps (21, 22) can have a simple straight tube structure, which makes it possible to reduce the scale of the ultraviolet irradiation apparatus 1. For example, the first tubular body 25 of the first discharge lamp 21 and the second tubular body 26 of the second discharge lamp 22 each have a length in the Y direction of 15 mm to 200 mm and an outer diameter of 2 mm to 16 mm.

Further, the ultraviolet irradiation apparatus 1 includes the second discharge lamp 22 having a lower starting voltage (discharge starting voltage) than the first discharge lamp 21 that emits ultraviolet light. The second discharge lamp 22 is located near the first discharge lamp 21 and therefore functions as a starting assistance because the first tubular body 25 of the first discharge lamp 21 is irradiated with visible light emitted from the second discharge lamp 22 so that the time before the first discharge lamp 21 lights up can be reduced.

Further, such a structure as described above makes it possible to extract part of visible light emitted from the second discharge lamp 22 from the light irradiation window 15 through the gap y1 between the first electrode block 31 and the second electrode block 32. Similarly to the first discharge lamp 21, the second discharge lamp 22 is configured to emit light by the application of a voltage through the electrode blocks (31, 32). Therefore, when visible light emitted from the second discharge lamp 22 is confirmed to be shining through the light irradiation window 15, it means that voltage is also being applied to the first discharge lamp 21, and it can be apparently regarded as ultraviolet light being emitted from the first discharge lamp 21. This allows a user to recognize that ultraviolet light is being emitted through the light irradiation window 15 by viewing the visible light emitted from the second discharge lamp 22 through the light irradiation window 15.

OTHER EMBODIMENTS

Hereinbelow, other embodiments will be described.

Figure 16A:
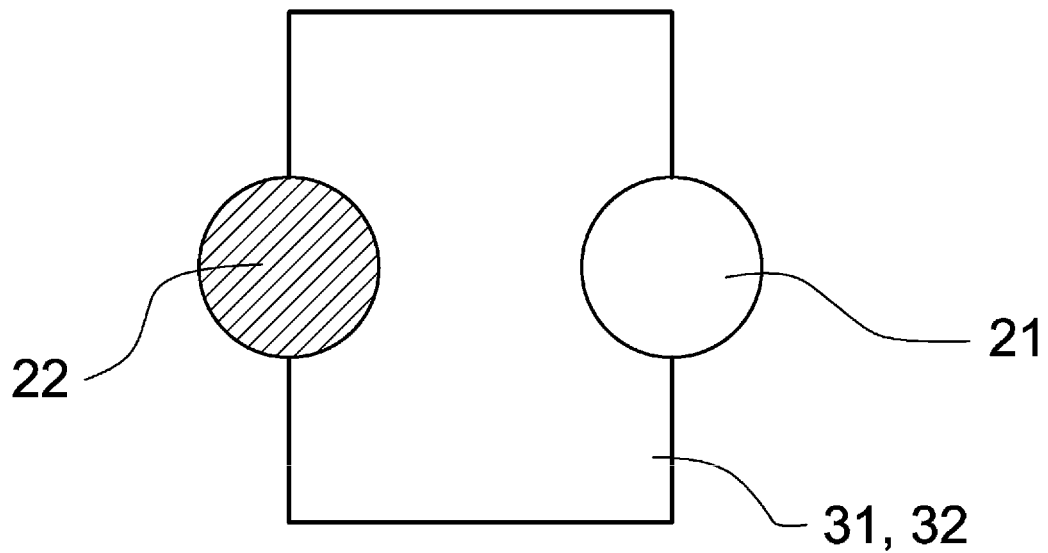
FIG. 16A is a diagram schematically showing the positional relationship between electrode blocks and discharge lamps of a ultraviolet irradiation apparatus according to another embodiment.
Figure 16B:
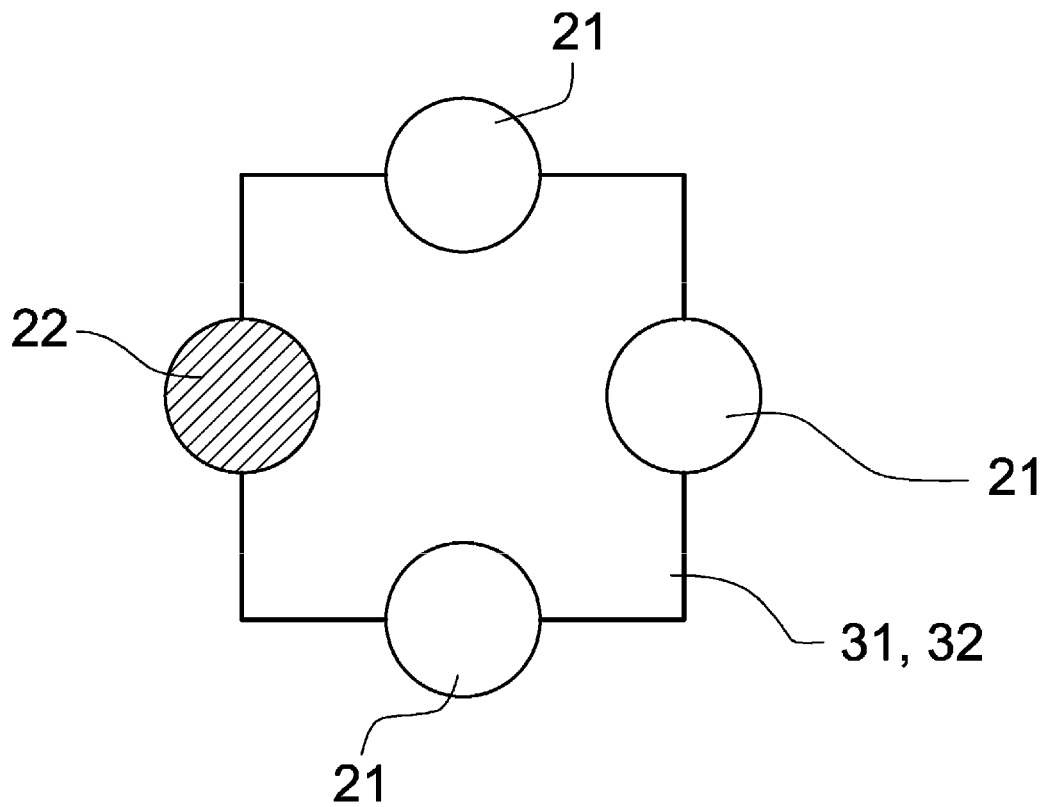
FIG. 16B is a diagram schematically showing the positional relationship between electrode blocks and discharge lamps of a ultraviolet irradiation apparatus according to another embodiment.

<1> The number of the first discharge lamps 21, the number of the second discharge lamps 22, and the arrangement of the discharge lamps in the ultraviolet irradiation apparatus 1 may freely be set. For example, as shown in FIG. 16A, the ultraviolet irradiation apparatus 1 may have one first discharge lamp 21 and one second discharge lamp 22 provided on opposite side surfaces of each of the electrode blocks (31, 32), respectively. Alternatively, as shown in FIG. 16B, the second discharge lamp 22 may be provided on one of four side surfaces of each of the electrode blocks (31, 32), and the first discharge lamps 21 may be provided on the remaining three side surfaces. In the case of the structure shown in FIG. 16B, the ultraviolet irradiation apparatus 1 may have light irradiation windows 15 provided in the three surfaces. This allows ultraviolet light to be extracted in multiple directions, making the structure easier to use for sterilization/deodorization applications in a given space, for example, sterilization/deodorization of the inside of shoes.

It is to be noted that the electrode blocks (31, 32) do not necessarily need to have a rectangular shape when viewed from the Y direction, and may have any shape such as a polygonal shape or a circular shape.

Figure 17:
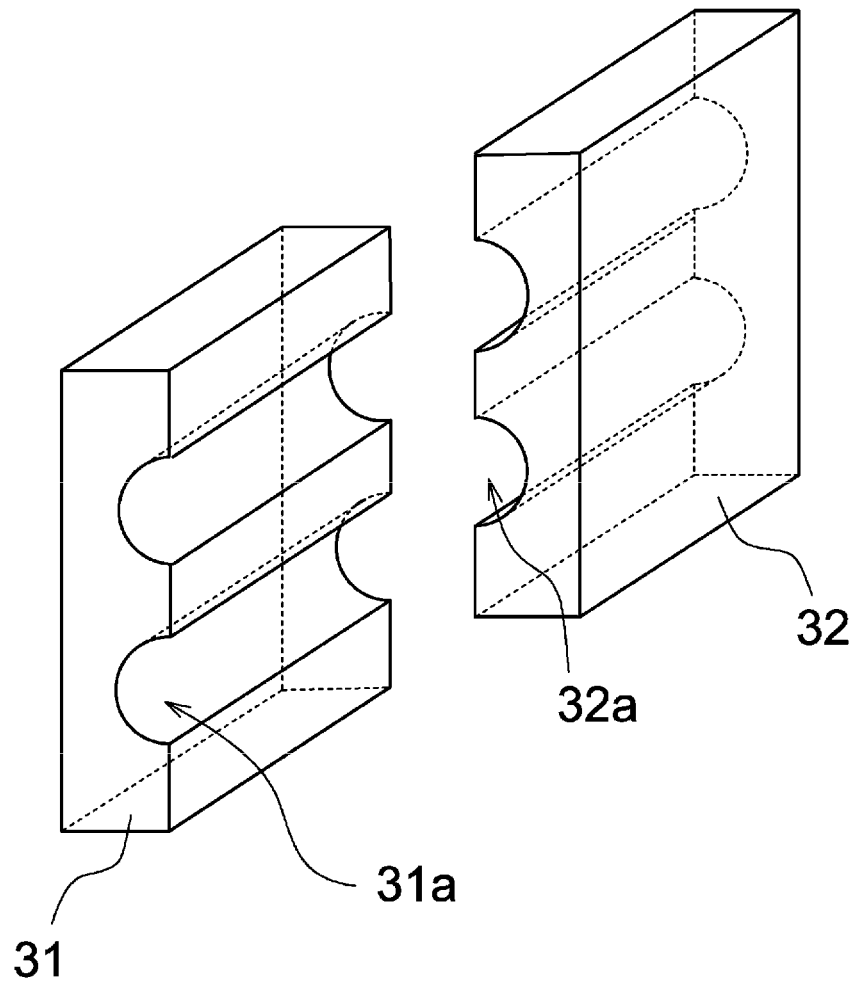
FIG. 17 is a perspective view schematically showing the structure of electrode blocks of a ultraviolet irradiation apparatus according to another embodiment.
Figure 18:
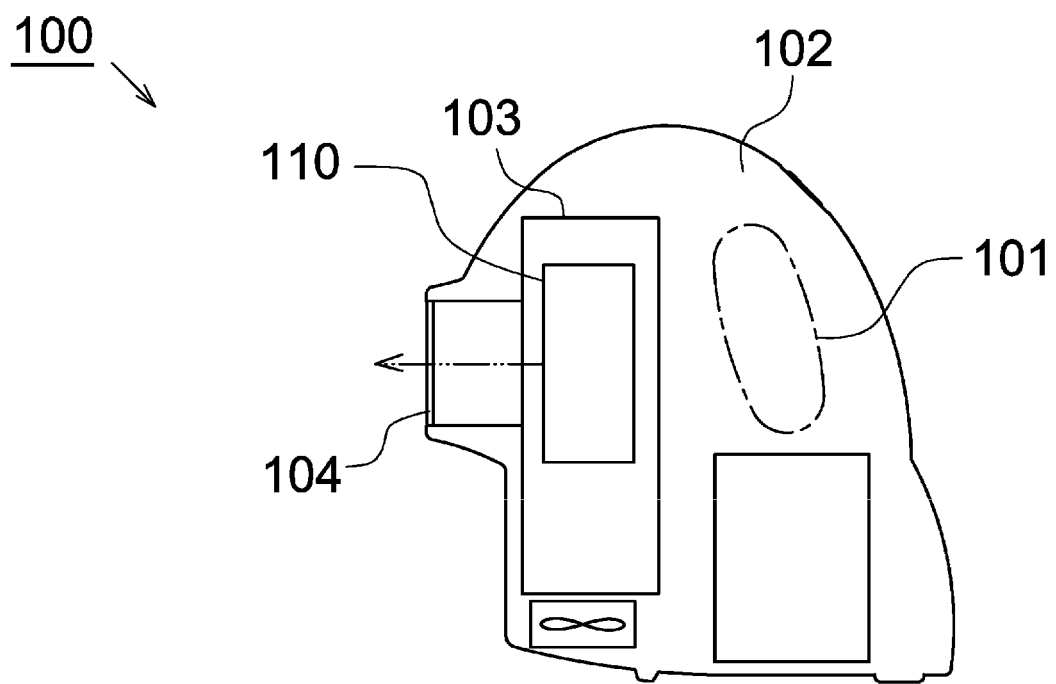
FIG. 18 is a diagram schematically showing the structure of a conventional small ultraviolet irradiation apparatus.
Figure 19:
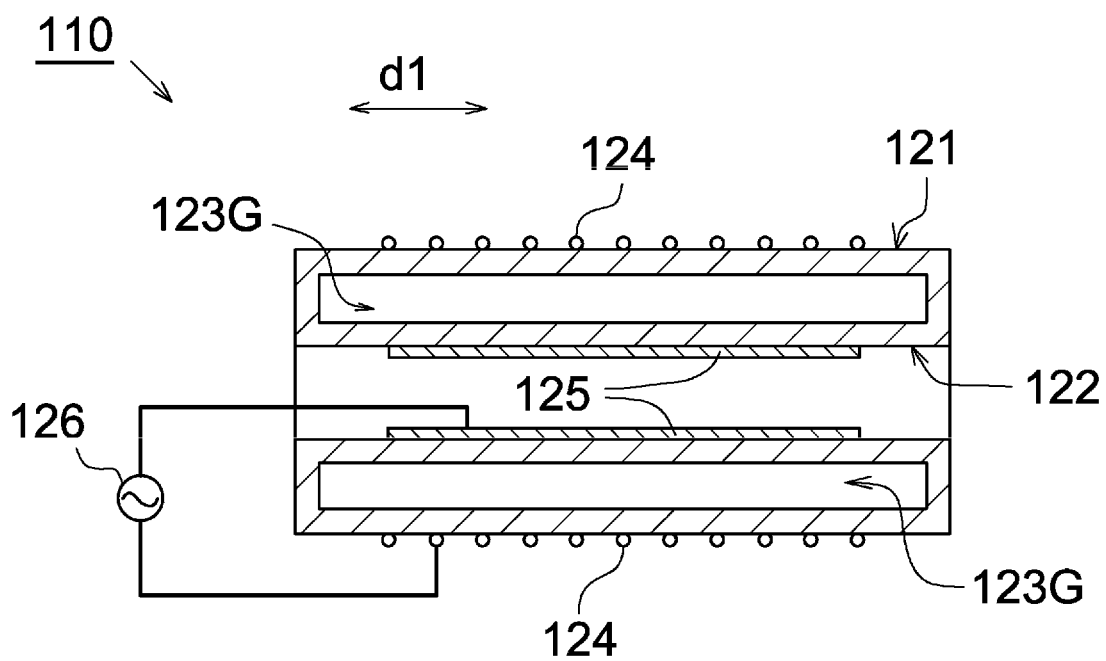
FIG. 19 is a diagram schematically showing the structure of an excimer lamp included in the ultraviolet irradiation apparatus shown in FIG. 18.

<2> As shown in FIG. 17, the first recessed grooves 31a may be formed on the +X-side side surface of the first electrode block 31 while the third recessed grooves 32a are formed on the −X-side side surface of the second electrode block 32. That is, the discharge lamps (21, 22) may be placed so as to be fitted in recessed grooves formed in the +X-side side surface of one of the electrode blocks and recessed grooves formed in the −X-side side surface of the other electrode block. In this case, however, the ultraviolet irradiation apparatus 1 preferably includes light irradiation windows 15 provided in both the +X-side side surface and −X-side side surface of the casing member 3.

<3> The above embodiment has been described with reference to a case where the first electrode block 31 and the second electrode block 32 are located apart from each other in the Y direction. However, the first electrode block 31 and the second electrode block 32 may be joined together through an insulating member.

In this case, however, since the gap y1 shown in FIG. 6 is not present, there is a possibility that visible light emitted from the second discharge lamp 22 will not be extracted at a visible light level through the light irradiation window 15 as a result of being blocked by the electrode blocks (31, 32). In such a case, the ultraviolet irradiation apparatus 1 may include also a light irradiation window for extracting visible light separately provided in the −X-side side surface of the casing member 3.

<5> The above embodiment has been described with reference to a case where both the first electrode block 31 and the second electrode block 32 are made of a conductive metallic member. However, both the electrode blocks (31, 32) may be made of an insulating material while conductive sheet members are provided in regions to which the current-carrying members (51, 52) are connected and contact regions with the tubular bodies (25,26) of the discharge lamps (21, 22) (i.e., the first electrode region to the fourth electrode region).

<5> Each of the discharge lamps (21, 22) may be located across the first electrode block 31, the second electrode block 32, and another block provided between the first electrode block 31 and the second electrode block 32.

<6> The above embodiment has been described with reference to a case where the ultraviolet irradiation apparatus 1 includes the second discharge lamp 22 that emits visible light. However, the present invention does not exclude the ultraviolet irradiation apparatus 1 that includes only the first discharge lamps 21 that emit ultraviolet light without including the second discharge lamp 22.

<7> The structures of the ultraviolet irradiation apparatus 1 described above with reference to the drawings are merely examples, and the present invention is not limited to the structures shown in the drawings. For example, the ultraviolet irradiation apparatus 1 may omit the holding members (46, 47) and the fixation screws (48, 49).

DESCRIPTION OF REFERENCE SIGNS

1 Ultraviolet irradiation apparatus
3 Casing member
5 Power button
7 Battery
9 Battery holder
10 Power supply part
10*a* First terminal
10*b* Second terminal
11 Electrical body
13 Electrical body holder
15 Light irradiation window
17 Lamp holder
21(21*a*, 21*b*) First discharge lamp
21G First discharge gas
22 Second discharge lamp
22G Second discharge gas
25 First tubular body
26 Second tubular body
31 First electrode block
31*a*, 31*b* First recessed groove
31*c* Second recessed groove
32 Second electrode block
32*a*. 32*b* Third recessed groove
33*c* Fourth recessed groove
41 First wire
42 Second wire
43 First screw member
44 Second screw member
46, 47 Holding member
46*a*, 47*a* Lamp presser
48, 49 Fixation screw
51 First current-carrying member
52 Second current-carrying member
61 First electrode region
62 Second electrode region
63 Third electrode region
64 Fourth electrode region
100 Conventional ultraviolet irradiation apparatus
101 Gripper
102 Housing
103 Lamp holder
104 Light irradiation window
110 Excimer lamp
121 Outer tube
122 Inner tube
123G Discharge gas
124 Outer electrode
125 Inner electrode
126 Power supply part
y1 Gap

The invention claimed is:

1. An ultraviolet irradiation apparatus comprising:
a first electrode block and a second electrode block located apart from each other in a first direction or located in an electrically-insulated state in the first direction;
a recessed groove formed on a side surface of each of the first electrode block and the second electrode block extending in the first direction;
a first discharge lamp including an excimer lamp, partially fitted into the recessed grooves formed in both the first electrode block and the second electrode block, and located across the first electrode block and the second electrode block extending in the first direction;
a power supply part for supplying electrical power to the first discharge lamp;
a first current-carrying member that electrically connects the first electrode block and the power supply part;
a second current-carrying member capable of electrically connecting the second electrode block and the power supply part at an electrical potential different from that of the first current-carrying member; and
a light irradiation window for extracting ultraviolet light emitted from the first discharge lamp to outside, the light irradiation window being formed in a side of the first discharge lamp opposite from the first electrode block and in a side of the first discharge lamp opposite from the second electrode block, wherein
the first discharge lamp includes a tubular body filled with a first discharge gas containing a noble gas and a halogen gas, and
the recessed groove includes a shape fitted to the shape of side surface of the tubular body of the first discharge lamp.

2. The ultraviolet irradiation apparatus according to claim 1, wherein the first electrode block and the second electrode block are made of a metallic member having reflective properties for the light emitted from the first discharge lamp.

3. The ultraviolet irradiation apparatus according to claim 1,
wherein the first current-carrying member includes a first screw member inserted at a predetermined position into the first electrode block and a first wire connecting the first screw member to the power supply part, and
the second current-carrying member includes a second screw member inserted at a predetermined position into the second electrode block and a second wire connecting the second screw member to the power supply part.

4. The ultraviolet irradiation apparatus according to claim 1, wherein each of the first electrode block and the second electrode block has the recessed grooves formed in two or more positions apart from each other when viewed from the first direction, and
  a number of the first discharge lamps corresponds to a number of the recessed grooves formed in each of the first electrode block and the second electrode block.

5. The ultraviolet irradiation apparatus according to claim 1, further comprising a second discharge lamp having a lower starting voltage than the first discharge lamp, wherein
  each of the first electrode block and the second electrode block has the recessed grooves formed in two or more positions apart from each other when viewed from the first direction, and
  a number of the recessed grooves formed in each of the first electrode block and the second electrode block corresponds to a sum of a number of the first discharge lamps and a number of the second discharge lamps.

6. The ultraviolet irradiation apparatus according to claim 5, wherein the number of the first discharge lamps is equal to or larger than the number of the second discharge lamps.

7. The ultraviolet irradiation apparatus according to claim 5, wherein
  the second discharge lamp includes a tubular body filled with a second discharge gas capable of emitting visible light.

8. The ultraviolet irradiation apparatus according to claim 7, wherein the first discharge gas contains Kr and Cl, and the second discharge gas contains Ne.

9. The ultraviolet irradiation apparatus according to claim 1, wherein
  the power supply part includes a battery and an electrical component that transforms a voltage supplied from the battery, and
  the ultraviolet irradiation apparatus further comprises:
  a battery holder that houses the battery;
  an electrical component holder that is located in a position apart from the battery holder and houses the electrical component;
  a lamp holder that is located in a position apart from the battery holder and the electrical component holder, houses the first electrode block, the second electrode block, and the first discharge lamp, and has the light irradiation window formed in part thereof; and
  a casing member that houses the battery holder, the electrical component holder, and the lamp holder.

10. The ultraviolet irradiation apparatus according to claim 1, wherein
  at least a portion of the ultraviolet light emitted from the first discharge lamp travels toward the light irradiation window from the opposite side of where the first or second electrode block is located, as viewed from the tubular body of the first discharge lamp.

11. The ultraviolet irradiation apparatus according to claim 1, further comprising:
  a first holding member to hold the first electrode block and the first discharge lamp in a contact state; and
  a second holding member to hold the second electrode block and the first discharge lamp in a contact state, wherein
  the first and second holding members each include a presser member having a shape fitted to the shape of side surface of the tubular body.

12. The ultraviolet irradiation apparatus according to claim 1, wherein the first and second electrode blocks are located apart in the first direction, and
  both ends of the tubular body of the first discharge lamp protrude outward from the first and second electrode blocks with respect to the first direction.

13. The ultraviolet irradiation apparatus according to claim 10, further comprising:
  a first holding member to hold the first electrode block and the first discharge lamp in a contact state; and
  a second holding member to hold the second electrode block and the first discharge lamp in a contact state, wherein
  the first and second holding members each include a presser member having a shape fitted to the shape of side surface of the tubular body.

14. The ultraviolet irradiation apparatus according to claim 10, wherein the first and second electrode blocks are located apart in the first direction, and
  both ends of the tubular body of the first discharge lamp protrude outward from the first and second electrode blocks with respect to the first direction.

15. The ultraviolet irradiation apparatus according to claim 11, wherein the first and second electrode blocks are located apart in the first direction, and
  both ends of the tubular body of the first discharge lamp protrude outward from the first and second electrode blocks with respect to the first direction.

* * * * *